US00PP31923P3

(12) United States Plant Patent
Stemkens

(10) Patent No.: US PP31,923 P3
(45) Date of Patent: Jun. 30, 2020

(54) ***VERBENA* PLANT NAMED 'VEAZ0054'**

(50) Latin Name: *Verbena hybrida*
Varietal Denomination: VEAZ0054

(71) Applicant: SYNGENTA CROP PROTECTION AG, Basel (CH)

(72) Inventor: Henricus Godefridus Wilhelmus Stemkens, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/602,057

(22) Filed: Jul. 26, 2019

(65) Prior Publication Data

US 2020/0170165 P1 May 28, 2020

(51) Int. Cl.
*A01H 5/02* (2018.01)
*A01H 6/86* (2018.01)

(52) U.S. Cl.
USPC ..... Plt./308

(58) Field of Classification Search
USPC ..... Plt./308
CPC ..... A01H 5/02; A01H 6/86
See application file for complete search history.

(56) References Cited

PUBLICATIONS

PLUTO Plant Variety database Jan. 29, 2020. p. 1.*

* cited by examiner

*Primary Examiner* — Annette H Para
(74) *Attorney, Agent, or Firm* — Dale Skalla

(57) ABSTRACT

A new *Verbena* plant named 'VEAZ0054' particularly distinguished by large sized flowers, of which the upper 2 petals are purple colored and the lower 3 are lilac colored with white stripes, medium green, undivided leaves and a semi-upright and very vigorous plant habit.

1 Drawing Sheet

Latin name of the genus and species of the plant claimed: *Verbena hybrida.*

Varietal denomination: 'VEAZ0054'.

BACKGROUND OF THE NEW PLANT

The present invention comprises a new *Verbena*, botanically known as *Verbena hybrida*, and hereinafter referred to by the variety name 'VEAZ0054'.

'VEAZ0054' is a product of a planned breeding program. The new cultivar has large sized flowers, of which the upper 2 petals are purple colored and the lower 3 are lilac colored with white stripes, medium green, undivided leaves and a semi-upright and very vigorous plant habit.

'VEAZ0054' originated from a mutation found in May 2014 in a greenhouse in Enkhuizen, The Netherlands. The parent plant was an unpatented propriety plant named 'AU0341-1' having a bright purple color and even bigger flowers. One stem of this plant happened to have the indicated color.

'VEAZ0054' was selected as one flowering cutting of the stated plant in May 2014 and immediately reproduced.

The first act of asexual reproduction of 'VEAZ0054' was accomplished when vegetative cuttings were propagated in July 2014 in a greenhouse in Enkhuizen, The Netherlands.

BRIEF SUMMARY OF INVENTION

Horticultural examination of plants grown from cuttings of the plant initiated in the fall of 2014, and continuing thereafter, has demonstrated that the combination of characteristics as herein disclosed for 'VEAZ0054' are firmly fixed and are retained through successive generations of asexual reproduction.

'VEAZ0054' has not been observed under all possible environmental conditions. The phenotype may vary significantly with variations in environment such as temperature, light intensity, and day length.

A Plant Breeder's Right for this cultivar was applied for in the European Union on Nov. 22, 2018, No. 2018/3065. 'VEAZ0054' has not been made publicly available prior to the effective filing date of this application, notwithstanding any disclosure that may have been made less than one year prior to the effective filing date of this application by the inventor or another who obtained 'VEAZ0054' directly from the inventor.

The following traits have been repeatedly observed and are determined to be basic characteristics of the new variety. The combination of these characteristics distinguishes this *Verbena* as a new and distinct variety.

BRIEF DESCRIPTION OF THE PHOTOGRAPHS

Figure 1:
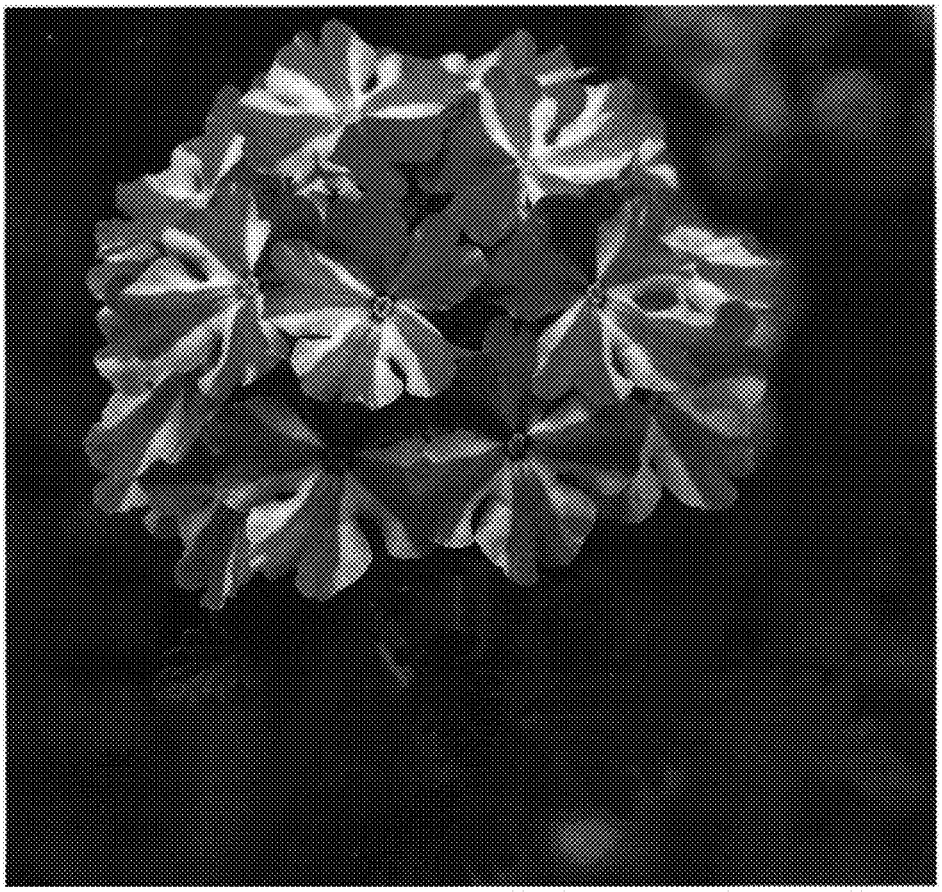
Figure 2:
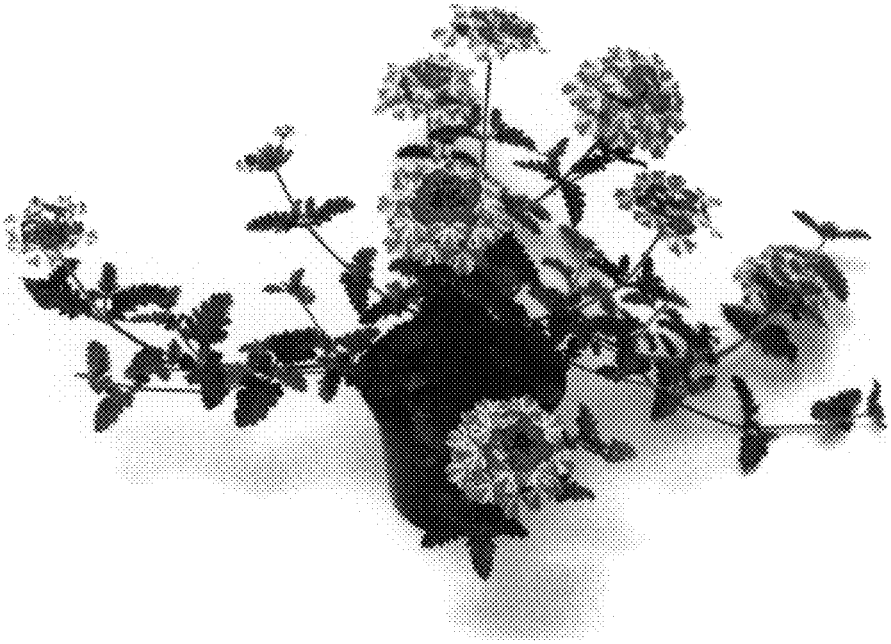

The accompanying photographic drawings show typical flower and foliage characteristics of 'VEAZ0054' with colours being as true as possible with an illustration of this type. The photographic drawing in FIG. 1 shows a close view of an inflorescence of the new plant, and in FIG. 2 a whole flowering plant.

The aforementioned photographs were taken in May 2018 in Andijk, The Netherlands. The plants were about 12 weeks old and were grown in 12 cm pots.

DETAILED BOTANICAL DESCRIPTION

Color references are made to The Royal Horticultural Society Colour Chart (R.H.S.) 2001.

TABLE 1

DIFFERENCES BETWEEN THE NEW VARIETY 'VEAZ0054' AND A MOST SIMILAR VARIETY

| | 'VEAZ0054' | 'VEAZ0019', U.S. Plant Pat. No. 26,438 |
|---|---|---|
| Flower color: | Lower petals star stripes white and lilac | Lower petals uniformly lilac |
| Flower, size: | Larger | Smaller |
| Plant, size: | Large | Small |

Plant:

*Form, growth and habit.*—Herbaceous, semi-trailing and vigorous.

*Plant height.*—22.0 cm.

*Plant height (inflorescence included).*—27.0 cm.

*Plant width.*—58.0 cm.

Roots:

*Number of days to initiate and produce roots.*—11-13 days at about 21 degrees C.

*Type.*—Fine, fibrous, free branching.

*Color.*—RHS N155B but whiter.

Foliage:

*Arrangement.*—Opposite, simple.

*Immature, leaf color, upper surface.*—RHS 144C.

*Immature, leaf color, lower surface.*—RHS 138B.

*Mature, leaf color, upper surface.*—RHS 144B.

*Mature, leaf color, lower surface.*—RHS 137C.

*Length.*—Approximately 3.8 cm.

*Width.*—3.2-3.5 cm.

*Shape.*—Hastate.

*Base shape.*—Obtuse.

*Apex shape.*—Obtuse.

*Margin.*—Lobed.

*Texture, upper surface.*—Pubescent.

*Lower surface.*—Pubescent.

*Color of veins, upper surface.*—RHS 145B.

*Color of veins, lower surface.*—145A.

*Pattern of veining.*—Pinnate.

*Petiole color.*—RHS 145B.

*Petiole length.*—0.7 cm.

*Petiole width.*—0.45 cm.

*Texture.*—Hirsute.

Stem:

*Branching characteristics.*—Side branches develop potentially at each node.

*Quantity of main branches per plant.*—16-20.

*Color of stem.*—RHS 144B.

*Stem length.*—27.0-36.0 cm.

*Stem width.*—0.3 cm.

*Length of internodes.*—2.4-3.2 cm.

*Texture.*—Hirsute.

*Color of peduncle.*—RHS 137C.

*Length of peduncle.*—2.4-4.2 cm.

*Peduncle diameter.*—0.2 cm.

*Texture.*—Glandular hairs.

Inflorescence:

*Type.*—Umbel-like, but actually a spike, umbrella shaped.

*Blooming habit.*—Flowers develop continuously during the summer months.

*Lastingness of individual blooms on the plant.*—About 3-4 days in the greenhouse.

*Fragrance.*—None.

*Number of inflorescences per plant.*—49 at various stages at development.

*Horizontal diameter of inflorescence.*—4.2-4.7 cm.

*Depth of inflorescence.*—3.8 cm.

*Number of florets and buds per inflorescence.*—Approximately 28-34.

Bud:

*Color.*—RHS N155A.

*Length.*—0.4 cm.

*Width.*—0.35 cm.

*Shape.*—Tubular with bulbous apex.

Floret:

*Form.*—Sessile; salver-shaped, composed of 5 partly fused petals with a base of a narrow tube.

*Immature color, upper surface.*—Upper 2 petals RHS N81B. Lower 3 petals RHS N82C with stripes RHS N155A.

*Immature color, lower surface.*—RHS N155A.

*Mature color, upper surface.*—Upper 2 petals RHS N81A. Lower 3 petals RHS N82B with stripes RHS N155A.

*Mature color, lower surface.*—RHS N155A.

*Floret diameter.*—5.6 cm.

*Floret length (depth).*—3.8 cm.

*Petal length.*—0.9 cm.

*Petal width.*—0.5 cm.

*Shape.*—Obcordate.

*Apex shape.*—Emarginate.

*Margin.*—Entire.

*Petal texture, upper surface.*—Smooth.

*Petal texture, lower surface.*—Smooth.

*Corolla tube length.*—2.3 cm.

*Corolla tube width.*—0.2 cm.

*Corolla tube color inside.*—RHS 47B.

*Tube color outside.*—RHS 47B.

*Corolla texture, inside.*—Pubescent.

*Corolla texture, outside.*—Canescent.

*Throat hair color.*—RHS 155C but whiter.

Calyx:

*Type.*—Five sepals whose margins are fused to each other along their length, with a transparent membrane of less than 0.1 cm in width and with one smaller sepal attached to the base of the calyx.

*Color of sepals.*—RHS 137B.

*Length of sepals.*—1.2 cm.

*Width of sepals.*—0.2 cm.

*Sepal shape.*—Fused, linear.

*Apex shape.*—Acute.

*Margins.*—Entire.

*Texture.*—Densely covered with very short glandular hair.

Reproductive organs:

Gynoecium:

*Pistil.*—1.

*Pistil length.*—1.4 cm.

*Style color.*—RHS 144C.

*Style length.*—1.6 cm.

*Stigma color.*—RHS 143A.

*Ovary color.*—RHS 144B.

*Ovary length.*—0.15 cm.

*Ovary width.*—0.1 cm.

Androecium:

*Stamens.*—Anthers and filaments fused to upper half of corolla tube; four anthers with two pollen sacs per anther.

*Color of filaments*.—RHS 151C.

*Filament length*.—0.2 cm.

*Anther color*.—RHS 151C.

*Anther length*.—0.1 cm.

*Pollen amount*.—None observed.

Fertility/seed set: Neither seed nor fruit production has been observed.

Disease/pest resistance: Resistance to pathogens and pests common to *Verbena* has not been observed.

What is claimed is:

1. A new and distinct variety of *Verbena* plant named 'VEAZ0054' substantially as illustrated and described herein.

* * * * *